(12) United States Patent
Conteas

(10) Patent No.: US 9,492,067 B2
(45) Date of Patent: *Nov. 15, 2016

(54) GASTROINTESTINAL LAVAGE SYSTEM

(71) Applicant: Chris N. Conteas, Northridge, CA (US)

(72) Inventor: Chris N. Conteas, Northridge, CA (US)

(*) Notice: Subject to any disclaimer, the term of this patent is extended or adjusted under 35 U.S.C. 154(b) by 134 days.

This patent is subject to a terminal disclaimer.

(21) Appl. No.: 13/906,875

(22) Filed: May 31, 2013

(65) Prior Publication Data

US 2013/0261394 A1    Oct. 3, 2013

Related U.S. Application Data

(60) Division of application No. 13/466,821, filed on May 8, 2012, now Pat. No. 8,496,611, which is a continuation of application No. 12/280,791, filed as application No. PCT/US2004/014575 on May 11, 2004, now Pat. No. 8,187,218, which is a continuation of application No. 10/638,213, filed on Aug. 7, 2003, now Pat. No. 6,939,293.

(51) Int. Cl.
*A61B 1/12* (2006.01)
*A61B 1/00* (2006.01)
(Continued)

(52) U.S. Cl.
CPC ............ *A61B 1/126* (2013.01); *A61B 1/00094* (2013.01); *A61B 1/00135* (2013.01);
(Continued)

(58) Field of Classification Search
CPC ................ A61M 2039/0279; A61M 3/0283; A61B 1/0051; A61B 1/126; A61B 1/31; A61B 17/3421; A61B 1/15; A61B 1/2736; A61B 1/00135; A61B 1/00094

USPC ....... 604/35, 43, 164.04; 600/121, 157, 158, 600/114

See application file for complete search history.

(56) References Cited

U.S. PATENT DOCUMENTS 3,894,540 A * 7/1975 Bonner, Jr. ........ A61M 25/0111
604/171
4,263,897 A     4/1981 Terayama
(Continued)

FOREIGN PATENT DOCUMENTS

| DE | 19756629 A1 | 9/1998 |
| JP | 55125301 U  | 9/1980 |
| WO | 0012148 A   | 3/2000 |

OTHER PUBLICATIONS

European Patent Office examination report, Oct. 27, 2014, 5 pages.
(Continued)

*Primary Examiner* — Imani Hayman
*Assistant Examiner* — Hamza Darb
(74) *Attorney, Agent, or Firm* — Fulwider Patton LLP

(57) ABSTRACT

An apparatus having a tube section and an expanded end. The tube section is flexible while the end section is rigid. The apparatus has a central bore, large enough to loosely receive an endoscope tube, and the end section has two peripheral bores which communicate with the central bore. There is a collar around the central bore which allows formation of air- and water-tight seal with the head of an endoscope. The tube may be fenestrated at its proximal end and may include medial pleats. This apparatus is mainly used by: sliding an endoscope into the central bore until the endoscope head forms an air- and water-tight seal with the central bore; connecting a lavage tube to one peripheral bore and a vacuum tube to the other peripheral bore; inserting the endoscope and the apparatus into a GI tract; and manually controlling the apparatus to apply lavage and vacuum.

2 Claims, 3 Drawing Sheets

(51) Int. Cl.
  *A61B 1/273* (2006.01)
  *A61B 17/34* (2006.01)
  *A61M 3/02* (2006.01)
  *A61B 1/31* (2006.01)
  *A61B 1/015* (2006.01)

(52) U.S. Cl.
  CPC .............. *A61B1/2736* (2013.01); *A61B 1/31* (2013.01); *A61B 17/3417* (2013.01); *A61B 17/3421* (2013.01); *A61M 3/0283* (2013.01); *A61B 1/015* (2013.01)

(56) References Cited

U.S. PATENT DOCUMENTS

| | | | |
|---|---|---|---|
| 4,573,965 A * | 3/1986 | Russo | A61M 27/00 604/128 |
| 4,795,424 A | 1/1989 | Burner | |
| 5,078,603 A | 1/1992 | Cohen | |
| 5,217,439 A * | 6/1993 | McClusky | 604/275 |
| 5,368,017 A * | 11/1994 | Sorenson et al. | 128/200.26 |
| 5,386,817 A | 2/1995 | Jones | |
| 5,409,469 A | 4/1995 | Schaerf | |
| 5,620,408 A | 4/1997 | Vennes et al. | |
| 5,658,238 A | 8/1997 | Suzuki et al. | |
| 5,807,240 A | 9/1998 | Muller | |
| 5,827,177 A | 10/1998 | Oneda et al. | |
| 5,876,329 A | 3/1999 | Harhen | |
| 6,086,542 A | 7/2000 | Glowa et al. | |
| 6,149,633 A | 11/2000 | Maaskamp | |
| 6,187,346 B1 | 2/2001 | Neuwirth | |
| 6,203,493 B1 | 3/2001 | Ben-Haim | |
| 6,322,495 B1 | 11/2001 | Snow et al. | |
| 6,419,654 B1 | 7/2002 | Kadan | |
| 6,428,510 B1 | 8/2002 | Kadan | |
| 6,447,473 B1 | 9/2002 | Levine | |
| 6,461,294 B1 | 10/2002 | Oneda et al. | |
| 6,520,951 B1 | 2/2003 | Carrillo, Jr. et al. | |
| 6,712,757 B2 | 3/2004 | Becker et al. | |
| 6,790,173 B2 * | 9/2004 | Saadat et al. | 600/114 |
| 6,808,492 B2 | 10/2004 | Snyder | |
| 6,869,393 B2 | 3/2005 | Butler | |
| 7,056,284 B2 | 6/2006 | Martone et al. | |
| 7,318,814 B2 | 1/2008 | Levine et al. | |
| 8,088,063 B2 | 1/2012 | Fujikura et al. | |
| 8,187,218 B2 * | 5/2012 | Conteas | 604/35 |
| 2002/0147385 A1 | 10/2002 | Butler et al. | |
| 2002/0188175 A1 | 12/2002 | Levine et al. | |
| 2005/0096503 A1 | 5/2005 | Conteas | |
| 2005/0124856 A1 | 6/2005 | Fujikura et al. | |
| 2006/0111611 A1 | 5/2006 | Eizenfeld et al. | |
| 2006/0270900 A1 | 11/2006 | Chin et al. | |
| 2007/0142709 A1 | 6/2007 | Martone et al. | |

OTHER PUBLICATIONS

US Endoscopy Brochure re: new product entitled Guardian Overtubes, Nov. 1, 2012.
European Search Report issued May 25, 2009, pp. 1-5.

* cited by examiner

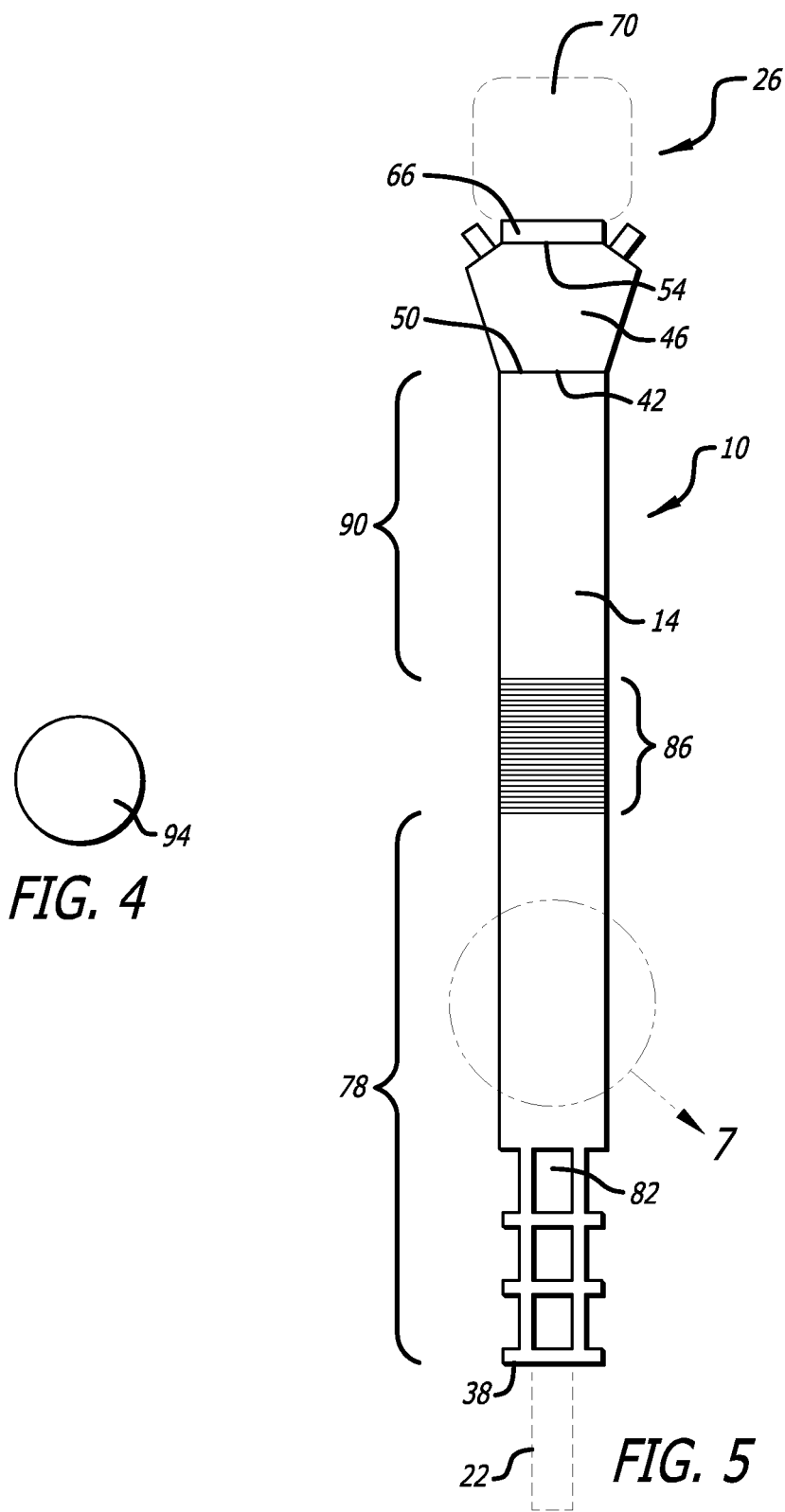

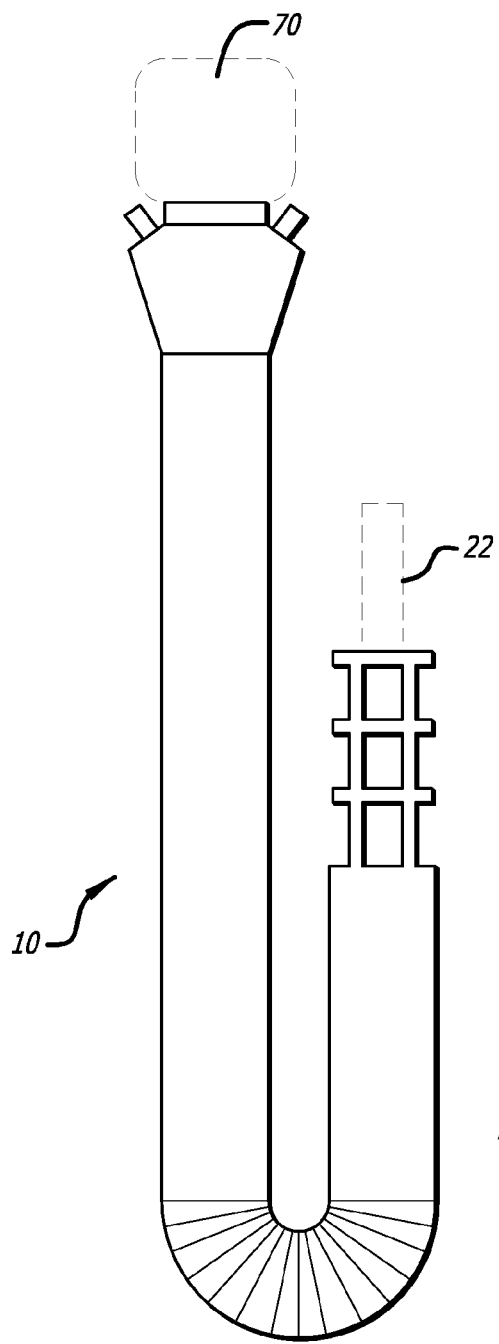
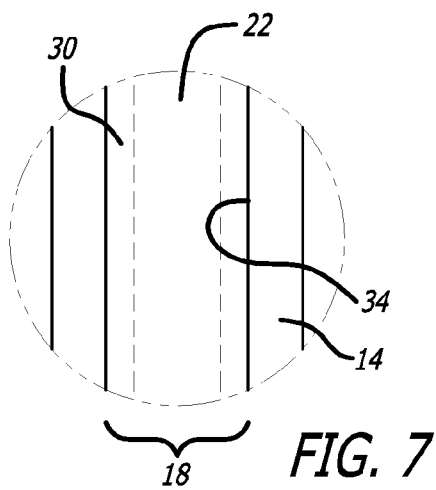
FIG. 6
FIG. 7

US 9,492,067 B2

GASTROINTESTINAL LAVAGE SYSTEM

RELATED APPLICATIONS

This is a divisional of application Ser. No. 13/466,821, filed on May 8, 2012, now Pat. No. 8,496,611, which is a continuation of application Ser. No. 12/280,791, filed on Aug. 26, 2008, now U.S. Pat. No. 8,187,218, issued May 29, 2012, which is a U.S. national phase of PCT/US2004/014575 filed May 11, 2004, claiming priority from U.S. patent application Ser. No. 10/638,213, filed Aug. 7, 2003, now U.S. Pat. No. 6,939,293, issued Sep. 6, 2005.

TECHNICAL FIELD

This invention relates upper and lower GI (GI) endoscopy. More specifically, this invention is used in conjunction with an endoscope to enable GI lavage and vacuuming thus making endoscopy safer and more clinically effective.

BACKGROUND ART

Since its inception in the latter 1960's flexible GI endoscopy; first with a miniature film camera, then with fiber optic bundles to carry the incident image and finally culminating in video chip technology, has evolved from a mechanical curiosity to a proven life-saving system for diagnosis and therapy. Many structures previously considered to be beyond diagnostic evaluation and therapeutics by any modality short of surgery are now open to the GI endoscopist: esophagus, stomach, duodenum, small intestine, biliary tree and pancreatic system are now accessible without use of an open surgical technique.

Endoscopic techniques can treat and palliate conditions such as stopping of GI bleeding, polyp removal, gallstone removal, stricture dilation, foreign body removal, endoscopic stint placement for GI obstruction and a host of other procedural capabilities too numerous to mention. The lesser morbidity and mortality with endoscopic procedures allows their use on sicker, more debilitated patents, increasing the clinical utility of endoscopic therapy.

While endoscopic diagnosis and therapy has opened many new avenues of GI care, some of its design strengths produce some of its greatest limitations. The endoscope is a flexible tube less than 1 cm in diameter, generally possessing one hollow bore through which instruments for injection of dye or haemostatic materials, biopsy and polypectomy attachments, and haemostatic probes are passed. At the same time this bore is used for suctioning of secretions. The bore is approximately 2.6 to 2.8 mm in diameter and not conducive to removal of larger diameter foreign material or highly viscous substances such as clotted blood. Cleansing the endoscopic visual field to remove food, blood, secretions impacted food bolus or foreign body is often impossible using this small bore. A larger bore conduit is needed to correct this shortcoming. Since the endoscope itself really cannot be modified to rectify this shortcoming, an appliance to be used in conjunction with the endoscope would be the preferable alternative.

Frequently, certain appliances are used in conjunction with endoscopy to aid in its use for diagnosis and therapy. A long flexible fenestrated tube with an open proximal end is often used to clear the upper GI tract of blood, food, foreign materials and secretions. This device uses a vacuum system for the removal of these materials and either gravity flow or pressure system to instill lavage fluid into the GI tract to help remove these materials. This system cannot be used simultaneously with an endoscope but must be used independently and inserted blindly into the upper GI tract. A blind insertion may cause trauma to the respiratory tree with sometimes disastrous results. Repeated removal and replacement of the endoscope and lavage tube may also stimulate retching which can induce vomiting, aspiration of gastric contents and even severe bleeding, both serious complications. The least number of removal and replacement of tubes against the pharynx and esophagus, the better. Further complicating the process of alternating lavage and endoscopy is the fact that rapid bleeding in the GI tract is frequently too rapid and too difficult to clear to the point that an endoscope may be effectively used. A lavage tube may cause a fleeting improvement in the visualization of a bleeding site, but from the time of removal of the lavage tube to the time of reintroduction of the endoscope, continued bleeding can obscure both normal enteric architecture as well as the pathologic process precipitating the problem. A system which allowed simultaneous lavage and endoscopy would circumvent all these problems.

Removal of foreign bodies from the upper GI tract is another common problem with potentially serious consequences. Foreign bodies may produce pain, bleeding and obstruction in the GI tract. Endoscopic treatment of this problem may be hampered by the need to frequently remove blood, food and secretions either prior to or at the same time as endoscopic evaluation and therapy is performed. Endoscopic therapy must take into consideration not only proper preparation and endoscopic technique for foreign body removal, hemostasis, stricture and dilation but also safety issues such as the prevention of aspiration of GI contents and foreign bodies into the respiratory tree, and prevention of laceration of the duodenum, stomach, esophagus and pharynx. Complicating this issue is that while a flexible polymer plastic over tube through which the endoscope and foreign bodies can be inserted and removed thus protecting surrounding structures, no system yet exists which can perform the endoscopic function while simultaneously possessing the capability to lavage out blood, food and secretions which can complicate foreign body removal. This increases the level of difficulty in their removal as well as increases potential complications in the removal process, such as aspiration and perforation. The ability to simultaneously see the GI tract while removing a foreign body would be a tremendous advantage over the system presently used.

Treatment of acute lower GI bleeding is complicated by the frequent obscuration of the bleeding site by blood, mucus and stool thus seriously limiting the utility of therapeutic colonoscopy for the acute treatment of lower GI bleeding. If blood, secretions and stool could be effectively and simultaneously removed while performing the colonoscopy, colonoscopy would be a more effective acute diagnostic and therapeutic interventional system than it is at the present time. This would save time in that a colonoscopy could be performed without the need to perform preceding colonic cleansing using either oral osmotic cathartics or enema which takes both precious time and involves increased risk in the patient who is semiconscious and hypotensive. The logistics in the typical medical center favors endoscopic intervention over the more involved and potentially more risky interventional angiography.

A system is needed which can cleanse and remove blood, foreign material, secretion and stool from the upper and lower GI tracts while simultaneously performing diagnostic and therapeutic endoscopy for hemostasis and removal of impacted material. The system must be capable of protecting GI structures from trauma and the respiratory system from aspiration of secretions, blood and foreign material.

There have been a number of developments in this area. U.S. Pat. No. 4,795,424 (Burner) concerns an apparatus for controlled irrigation of the natural cavities of the human body. It is characterized by a correcting means for equalizing the measuring signal, which represents the pressure, which is emitted by a pressure gauge according to the pressure losses and according to the differential pressure between it and the measurement of the pressure in the intervention area which corresponds to an organ. These correcting means include a correcting circuit adapted to effect a correction according to said pressure differential and a correcting circuit adapted to take into account the pressure loss, namely the flow rate of the fluid injected through the inner duct of the endoscope and the cross section of this duct.

This is an electrical system, designed principally for urologic endoscopy, for monitoring flow of fluid into and out of a small space by monitoring changes in pressure in the system. This is not a lavage system but a pressure-monitoring device for fluid entering and exiting a space. This could be used in the bladder or uterus for surgery to gauge fluid flow—it has nothing to do whatever with lavage of blood, food, dilation of strictures and, removal of foreign bodies. This is for measuring/monitoring and not effecting a change.

U.S. Pat. No. 5,030,202 (Harris) discloses a lavage apparatus comprising a lavage fluid supply apparatus, a first catheter having a distal end for positioning in the uterus of an animal and a proximal end for communication with the lavage fluid supply, a pair of bilateral catheters connected to the proximal end of the first catheter for extending into respective horns of the uterus, and catheter locating means for locating the catheters in the uterus. The first catheter defines respective supply and drain lumens. The bilateral catheters each define respective lumens for fluid communication between the supply lumen and the interior of the respective uterine horn. The lavage fluid supply apparatus may include a pump for supplying lavage fluid under pressure. The supply may also include a lavage fluid storage tank for containing a volume of fluid, and a heater to maintain the temperature of the stored fluid within a predetermined range. For use in a gravid uterus, a drain tube may be provided at the distal end of the first catheter for reaching into the depths of the uterus. Further, vacuum drainage apparatus may be provided to drain lavage fluid from the uterus. If desired, the lavage fluid supply may be utilized for purposes other than uterine lavages such as, for example, supplying fluids for intravenous infusion. It cannot be used for simultaneous endoscope and lavage in either the upper or lower gastrointestinal tract. Neither is it portable or disposable. One cannot effectively dilate and remove foreign material with this device.

U.S. Pat. No. 5,620,408 (Vennes et al.) discloses an endoscopic over-tube for receiving and guiding medical instrumentation into the upper alimentary canal of a patient. The endoscopic over-tube has a bite block for insertion and retention in the mouth of the patient. The endoscopic over-tube also has a flexible protective sheath engaging the bite block and adapted for insertion into the upper alimentary canal of the patient. The sheath includes a stiffened region that insulates the posterior wall of the patient's pharynx from medical instrumentation as the medical instrumentation is intubated through the sheath and into the patient's alimentary canal.

This tube is solely used to help an upper endoscopic bypass direct control of the pharynx by the endoscope protecting against irritation and gagging and possibly protecting the upper airway. The system is short and too rigid to be used for lavage. It cannot be sealed for lavage purposes. It cannot be moved when it is properly inserted. The new arrangement system is not as useful for lavage, hemostasis, foreign body removal, and dilation. It could not be used to simultaneously endoscope and lavage a patent, removing either blood, food or other foreign materials solely and expeditiously to accomplish the same procedure.

U.S. Pat. No. 5,827,177 (Oneda et al.) discloses an endoscope sheath assembly usable within an elongated flexible endoscope to isolate a portion of the endoscope from an external environment during a therapeutic or diagnostic endoscopic procedure. The sheath assembly has a sheath with an elongated flexible endoscope tube, a plurality of working bores extending the endoscope tube, and a low-friction, fabric isolating sleeve positioned within the endoscope tube and surrounding portions of the working bores. The isolating sleeve includes first and second sleeve lumens formed therein through which respective working bores extend. The coefficient of friction between the isolating sleeve and the working bores is less than the coefficient of friction between the working bores themselves so that working bores are frictionally isolated from each other, from the endoscope tube, and from the insertion tube to reduce resistance to articulation of the endoscope.

This is an endoscope with distensible elastomeric working bore within the endoscope tube for passage of instruments during diagnostic or therapeutic endoscopy. It is just a modified endoscope with the same failing described above: the bores are inadequate for removal of food, blood clots, passage of rigid dilators and removal of foreign bodies, let alone lavage and endoscopic treatment simultaneously.

U.S. Pat. No. 5,876,379 (Harben) discloses an endoscope for use with an elastomeric sheath for performing an endoscopic procedure. The endoscope includes a body, an insertion tube extending away from the body and terminating at a distal end portion, and a sheath retainer connected to the distal end portion of the insertion tube for releasably retaining the sheath on the insertion tube in a substantially fixed position during the endoscopic procedure. The sheath is an elastomeric member movable between a radially expanded position and a contracted position, and the sheath is biased toward the contracted position. The sheath retainer is a generally C-shaped member having a pair of retaining tabs spaced apart from each other and extending away from an outer surface of the insertion tube's distal end portion to define a working bore retaining area there between. The retaining tabs are positioned and sized to engage a portion of the sheath at its distal end portion and to prevent the distal end portion of the sheath from moving axially relative to the distal end portion of the insertion tube, particularly during an endoscopic procedure.

This is not a lavage system but an endoscope covered by a tight-fitting elastomer membrane keeping the visual system of the endoscope in close proximity to a biopsy-utility bore. This is just an endoscope tube composed of two pieces covered by an elastomeric sheath. It has the same failings of contemporary endoscopes: no ability to lavage, dilate or remove foreign bodies.

U.S. Pat. No. 6,149,633 (Maaskamp) discloses a system which utilizes an endoscope and irrigation fluid during surgery within a body orifice, and in which irrigation fluid is withdrawn via a principal path into a suction canister, there is a substantially constant suction and withdrawal rate from the operative site to limit absorption of irrigation fluid within the patient, because a bifurcated flow path that leads to the suction canister not only from the endoscope but also from a drain bag receiving overflow from the body orifice via a tailored drape includes a substantially greater flow impedance in the drain bag path. The common suction line joined to the endoscope line and the drain bag line draws a flow through the endoscope that predominates, to maintain substantially constant withdrawal of irrigation fluid via that path, and substantially eliminates the possibility of loss of suction.

This is a system to meter fluid into body cavities during laparoscopy and not endoscopy. It measures fluid going into the cavity and fluid coming out of the cavity to prevent fluid overload of patient during surgery. It has nothing to do a lavage of GI bleeding, dilation of stricture and removal of foreign bodies. It is solely a fluid-monitoring system.

U.S. Pat. No. 6,187,346 (Neuwirth) discloses a method and composition for effecting necrosis of a tissue lining of a mammalian body cavity, particularly a uterine endometrium, by introducing an applicator comprising a hysteroscope housing a first and a second catheter connected to a catheter into the uterus, distending the uterus by introducing CO2 gas under pressure, delivering a silver nitrate paste to the endometrium through the first catheter and allowing the paste to remain a sufficient amount of time to substantially cauterize the entirety of the tissue lining, particularly the endometrium and delivering an aqueous sodium chloride solution to the uterus through the second catheter thereby neutralizing the silver nitrate and rinsing the uterine cavity.

This system is a hysteroscope with two bores to one apply a silver nitrite paste to the lining of the uterus/endometrial and the second to supply a sodium chloride solution to the silver nitrite-treated area to neutralize it. This system is used to effect necrosis and chemical cauterization of tissue, neutralize the cauterizing substance and rinse tissue. It is not an addition to an endoscope for simultaneous lavage of blood, foreign material, dilation of stricture and removal of foreign bodies. It cannot be adapted to any endoscope of popular design. The system has the same faults as described in GI endoscopes previously described : the bores are too small, it is non-flexible, and has no ability to remove foreign bodies or dilate strictures. It is a low flow system, with no ability to endoscopically perform hemostasis, biopsy and tissue removal while simultaneously lavaging the cavity the system has been introduced into. All foreign material goes back through the bore which may close. Alternatively, the foreign material just runs out of the uterus into the vagina where it is either suctioned or just spills out of the vagina into a receptacle. This is not an option in the upper GI tract due to the fear of aspiration of fluid into the lungs.

U.S. Pat. No. 6,203,493 (Ben-Haim) discloses a locatable endoscope attachment including an attachment connectable to an insertion tube portion of an endoscope for determining the endoscope's position; and one or more sensors, fixedly positioned with respect to the attachment, which are used for determining the positions of the one or more sensors. Preferably, when the attachment is fixedly attached to the endoscope, the one or more sensors are distanced from elements of the endoscope which interfere with determining the positions of the one or more sensors. This system places a magnetic field position sensor on the surface of an endoscope to determine its location in the intestinal tract. It has nothing to do at all with endoscopic lavage or has any real direct therapeutic/interventional application.

U.S. Pat. No. 6,322,495 (Snow et al.) discloses a system to place an intestinal feeding tube visually through the abdominal wall of the subject and direct it down the GI tract. It is solely for visualizing the position of the proximate end of the system for purposes of placement. It is designed to not work with or need a regular endoscope and has no capabilities for lavage, hemostasis, foreign body removal, etc.

U.S. Pat. No. 6,428,510 (Kadan) discloses a system for performing a single portal diagnostic needle arthroscopy and lavage comprised of a hand piece having valves for irrigation and suctioning and a diagnostic cannula attached to the hand piece. An arthroscope is passed through the hand piece and the diagnostic cannula and allows the procedure to be performed through a single port of entry into the interior of the joint. The system includes a mobile cart with a camera and light system and a high-resolution monitor. An air compressor is the pressure source powering the individually controlled irrigation pumps which drive the irrigation fluid through an irrigation hose to the hand piece while a vacuum suction console provides suction for collection of fluid in canisters mounted on the mobile cart. The system includes a biopsy cannula that can be easily exchanged for the diagnostic cannula using an exchange rod. The biopsy cannula is comprised of a pair of piggyback bores, one for visualization, diagnosis, irrigation and suction, while the other is for insertion of a biopsy instrument or other surgical devices. The biopsy instrument is comprised of a thin, approximately 1 mm flexible shaft connected to a forceps configured jaw at the distal end for performing surgical procedures in the joint compartment. A ring handle configuration at the instruments proximal end controls the jaws. Both the diagnostic cannula and biopsy cannula have couplings that include an auxiliary valve for introducing medication and drugs into the joint compartment as well as for removal of sterile synovial fluid.

While a well-designed system for arthroscopy biopsy and cleaning of joint spaces, this design does not apply to a lavage system to be used via the GI tract. The system cannot be used for dilation or foreign body removal. The arthroscope and lavage system are really not separable and due to this and its construction a system using the diagram no matter how scaled up would have functional problems and clogging with mucus, blood, food and other foreign material. This will obviate its effectiveness.

U.S. Pat. No. 6,461,294 (Oneda et al.) discloses an apparatus and methods for attaching and forming enclosed inflatable members on an endoscope assembly with a disposable sheath are disclosed. In one embodiment, an apparatus includes a flexible and resilient cuff member that is positioned on the outer surface of the disposable sheath and sealably and fixedly bonded to the sheath cover material at the cuff edges to form an annular space capable of being inflated. The inflatable member formed thereby is inflated through a lumen internal to the sheath that has an opening into the interior annular space. In another embodiment, the annular space may be divided into separate inflatable lobes. In still another embodiment, the cuff member is a flexible and resilient member that is substantially toroidal in shape that is positioned on the outer surface of the sheath. In a further embodiment, the inflatable member is formed from an excess length of sheath cover material disposed on the disposable sheath. A single reentrant fold of sheath material is formed with an edge that is sealably and fixedly bonded to the sheath cover material to form an annular space capable of inflation. In alternate embodiments, the excess length of cover material may be used to form members with dual reentrant folds that comprise inflatable members with single and dual inflatable lobes.

This is an inflatable outer elastomeric sheath to hold a bronchial endoscope in proper position for bronchial biopsy. It has nothing to do with endoscope lavage, etc.

U.S. Pat. No. 6,520,951 (Carillo, Jr. et al.) discloses a single operator exchange biliary catheter having a common distal lumen. The biliary catheter includes an elongate shaft having a proximal portion defining an ancillary lumen and a distal portion defining a common guide wire and ancillary lumen. The common distal lumen reduces the profile of the distal portion of the shaft. The elongate shaft also includes a proximal guide wire port disposed between the proximal end of the shaft and the distal end of the shaft to facilitate single operator use. A seal may be disposed adjacent the proximal guide wire port to thereby seal the port. Preferably, the shaft includes a single lumen distal portion and a bilumen proximal portion. The single lumen distal portion of the shaft may be curved and may include a tapered or spherically shaped distal tip.

This is an easily exchanged biliary catheter used to stint bile duct strictures for trist obstruction. It is more easily placed and exchanged. It has nothing to do with endoscopic lavage, foreign body retrieval, dilation and cannot be used simultaneously with an endoscope.

The systems presently in use and described above are inadequate due to certain inherent disadvantages:

A) The only bores presently available in all endoscopes commonly used in clinical practice are woefully too narrow to accommodate very viscous or large solid materials, making their removal impossible.

B) No system exists specifically adapted for endoscopes, either upper or lower, to allow simultaneous instillation of solubilizing lavage fluid with its subsequent removal by a vacuum system while performing endoscopic visualization and manipulation of GI structures.

C) Foreign bodies, large chunks of meat or vegetables cannot be removed by lavage systems in general use. Nor do these systems allow for endoscopic visualization of the bolus while it is being removed.

D) Flexible tubes used to remove harmful foreign bodies by producing a shielded bore through which the material is removed without risk of injury to surrounding structures (GI and respiratory) do not have lavage capability.

E) No endoscopic lavage system is as yet produced which can function with or without the endoscope in place.

F) No such system such as described in E) exists which can be used to dilate strictures in the GI tract using either flexible or balloon dilators.

G) No endoscopic lavage system exists which can be used concomitantly with endoscopic visualization of the lower GI tract (i.e., colon). The system would not only remove blood and mucus from the GI tract, but also any and all fecal material which may be obscuring the vision of the endoscopist.

H) No such system described in G) exists which may be used independently of the endoscope to draw gas and fluids from the lower GI tract. This could be very important in the treatment of such conditions as ileus or volvulus, where temporary colonic decompression by colonoscope is frequently used for acute intervention but prolonged decompression might be of greater clinical advantage.

I) The use of laser therapy to open areas of the GI tract closed by cancer sometimes produces smoke from the burned flash which can both occlude the view of the procedural area and also produce a noxious smell. An endoscopic vacuum system would be useful for the removal of offending gases and help to maintain a clear operative field. No such system is presently available.

Development of a system which can cleanse and remove blood, foreign material, secretion and stool from the upper and lower GI tracts while simultaneously performing diagnostic and therapeutic endoscopy for hemostasis and removal of impacted material represents a great improvement in the field of endoscopy and satisfies a long felt need of the gastroenterologist.

DISCLOSURE OF INVENTION

The present invention is an apparatus having a tube section with a proximal end and, connected to the tube, an expanded end section or housing with a distal end. The expanded end section is preferably made of plastic and adapted for insertion of an endoscope. The tube section is flexible and adapted to slide into the GI tract and the expanded end section is rigid. Preferably, the apparatus has a central bore there through and the expanded end section has two peripheral bores which communicate with the central bore within the expanded end section. The central bore is large enough to loosely receive an endoscope tube. There is a collar around the central bore at the distal end which adapts the end section to form an air- and water-tight seal with the head of an endoscope. The expanded end section also has fittings designed to connect tubing to the peripheral bores.

In an alternative embodiment, the tube has a central bore there through and the expanded end section or housing is hollow. The central bore is large enough to loosely receive an endoscope tube. There is a collar at the distal end which adapts the end section to form an air- and water-tight seal with the head of an endoscope. The collar has a central bore of the same size as and axially aligned with the central bore through the tube. The expanded end section also has fittings designed to connect tubing to the hollow center.

The tube may be fenestrated at its proximal end.

This apparatus is used by: sliding an endoscope, tube first, into the central bore(s) until the endoscope head forms an air- and water-tight seal with the central bore through the collar; connecting a lavage tube to one fitting; connecting a vacuum tube to the other fitting; inserting the endoscope and the apparatus into a GI tract; and manually controlling the apparatus with visual feedback from the endoscope to apply lavage and vacuum where and as needed within the GI tract.

A cap adapted to form an air- and water-tight seal to the collar may also be provided. In this case the apparatus is used by: turning off the lavage and vacuum; removing the endoscope from the central bore(s); capping the collar and thus the central bore(s) with the cap; and turning on the lavage and vacuum.

Alternatively, the apparatus may be used by: turning off the lavage and vacuum; removing the endoscope from the central bore(s); attaching a lavage or vacuum tube to the central bore(s); and turning on the lavage and vacuum thus producing a high volume lavage system capable of removal of solids and liquids.

Several objectives and advantages of this present invention are:

A) A system to provide optimum removal of blood, food, secretions and other material from the GI tract leaving the bores of the endoscope free to be used for their primary role as a conduit for diagnostic and therapeutic devices.

B) A system which will allow for simultaneous instillation of solubilizing lavage fluid with subsequent removal by vacuum extraction while performing endoscopy.

C) A system which can be used for removal of foreign bodies, large chunks of meat or vegetable material.

D) A system to remove harmful foreign bodies from the GI tract without injury to the GI tract of the patient or respiratory tract as well.

E) A system capable of being used with or without the endoscope.

F) A system capable of use in the lower GI tract simultaneously incorporating lavage with endoscopic examination and manipulation.

G) A system capable of being used independently of the endoscope in the lower GI tract for removal of solids, liquids and gas for treatment of ileus or volvulus H) A system to remove gas, blood and secretions from the GI tract while performing laser therapy.

An appreciation of the other aims and objectives of the present invention and an understanding of it may be achieved by referring to the accompanying drawings and description of a preferred embodiment.

BRIEF DESCRIPTION OF DRAWINGS

FIG. 4 is an end view of the plug for plugging the large central bore.

FIG. 5 is a side view of this invention with the endoscope fully inserted.

FIG. 6 is a view of this invention turned about 180° with the endoscope fully inserted illustrating the flexibility of the invention.

FIG. 7 is an enlarged view of the area outlined at 7 on FIG. 5.

BEST MODE FOR CARRYING OUT INVENTION

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
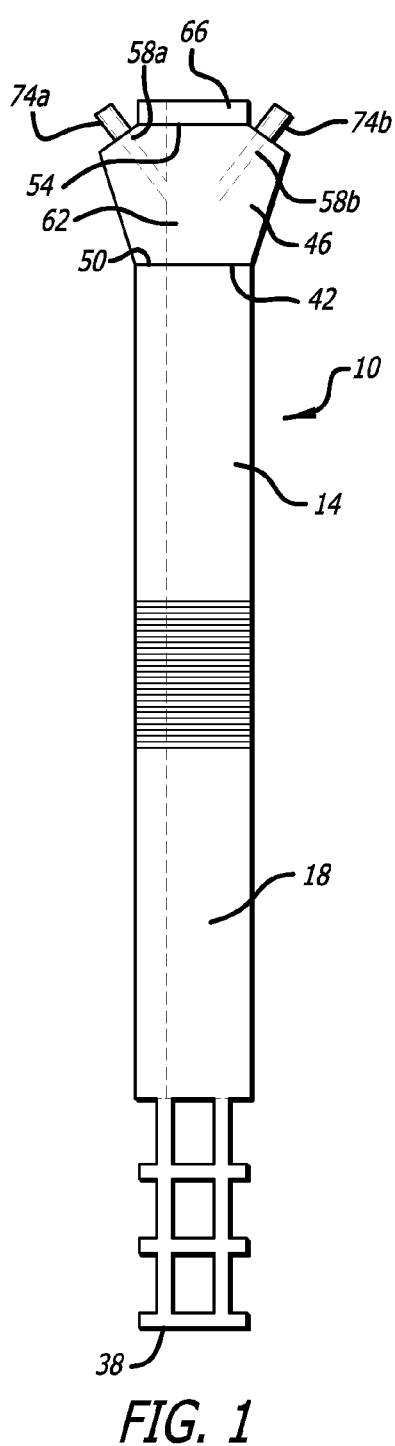
FIG. 1 is side view of this invention completely straight.
Figure 1A:
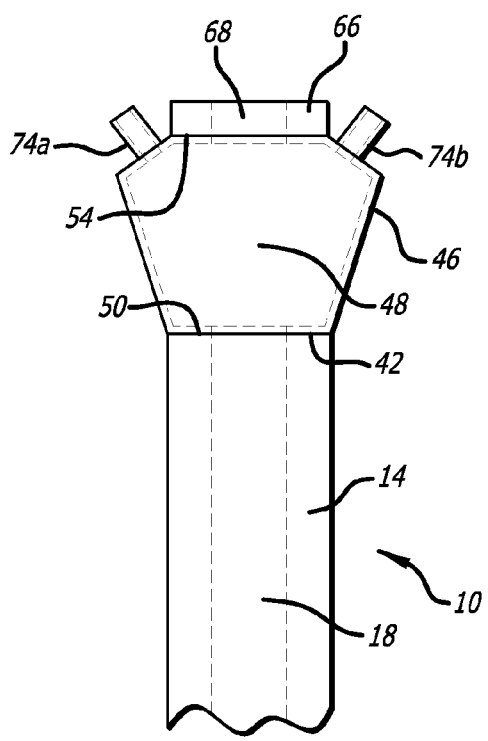
FIG. 1A is a partial side view of the distal end of an alternate embodiment of this invention.
Figure 2:
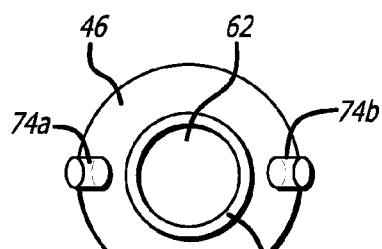
FIG. 2 is a view of this invention from the distal end.
Figure 3:
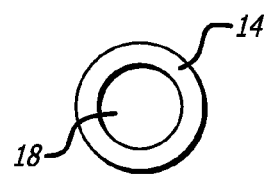
FIG. 3 is a view of this invention from the proximal end.

The preferred embodiment 10 of this invention is described in FIGS. 1 through 7. The invention 10 comprises a long tube 14 with a large central bore 18 through it. The tube 14 is constructed of a flexible, solvent, and acid-resistant plastic polymer. The central bore 18 is large enough to loosely contain the tube 22 of an endoscope 26. A loose fit is defined to mean that there is sufficient space 30 between the endoscope tube 22 and side 34 of the bore 18 to permit: injection of lavage fluid by a lavage system all the way to the proximal end 38 of the tube 14 and into the GI tract; and removal of this lavage fluid plus blood, mucus, particles, etc. from the GI tract by vacuum action.

The distal end 42 of the tube 14 is attached to a housing 46. The housing 46 is constructed of a hard, solvent, and acid-resistant plastic polymer. Attachment can be by any means that provide air and water tight joints. Alternatively, the housing 46 and tube 14 can be fabricated integrally. The housing 46 is the same diameter as the tube 14 at the proximal end 50 but of larger diameter at the distal end 54. There are three bores 58a, 58b, 62 through the housing 46. The large central one 62 mates with the central bore 18 through the tube 14 at the proximal end 50 and terminates in a rubber collar 66 at the distal end 54. This collar 66 provides an air- and water-tight seal when the endoscope head 70 is fully advanced into the housing 46. This collar 66 is also designed to mate with vacuum and lavage tubing of an appropriate size with an air and water-tight seal.

The two, smaller, peripheral bores 58a, 58b intersect the large central bore 62 within the housing 46 and terminate in fittings 74a, 74b at the distal end 54. The large bores 18, 62 through the tube 14 and housing 46 are adapted to loosely receive the tube 22 of an endoscope 26. The fittings 74a, 74b are adapted to mate with externally supplied fluid and vacuum lines.

In an alternative embodiment, the tube 14 has a central bore 18 there through and the housing 46 has a hollow center 48. The central bore 18 is large enough to loosely receive an endoscope tube. There is a collar 66 at the distal end 54 which adapts the housing to form an air- and water-tight seal with the head 70 of an endoscope. The collar 66 has a central bore 68 of the same size as and axially aligned with the central bore 18 through the tube 14. The housing 46 also has fittings 74a, 74b designed to connect tubing to the hollow center 48.

The reason the housing 46 expands in diameter from the proximal 50 to distal 54 end is to provide room for attachment of tubing to the fittings 74a, 74b.

The flexible tube 14 is uniquely constructed in three basic regions. The first and most proximal region 78 is a smooth with a number of fenestrations 82 beginning a short distance behind the proximal end 38 of the tube 14. This segment 78 is critical to the function of the system 10 as it allows easy entrance and egress of blood, food and foreign semisolids and lavage fluid even while the endoscope 26 is in position. Frontal and radial positioning of openings 82 allows not only an easier passage of fluids but makes it less likely that the covering of a few of the openings by GI mucosa or extraneous material would seriously impede the function of the invention 10.

The second segment 86 of the tube 14 is accordion-pleated to allow for both optimal flexibility and strength so as to prevent collapse of the bore 18 within the tube 14 while it is flexed or under vacuum (negative pressure). This pleating is constructed as to not compromise the desired inner diameter of the tube 14. The pleating allows the invention to flex backwards up to almost 180° as illustrated in FIG. 6.

The third segment 90 of the tube 14 is again smooth.

A separate polymer plastic cover 94, as illustrated in FIG. 4, for the endoscope docking collar 66 allows the invention to be used without the endoscope 26 in place. The cover is designed to provide a water- and air-tight seal.

The peripheral bores 74a, 74b are used for vacuum extraction of blood, food and sections, and instillation of lavage fluid even without the endoscope 26 in place due to a now larger effective bore in the flexible tube 14 and housing 46 in the absence of the endoscope 26.

In light of the previous descriptions, a number of advantages of this system 10 for its use with and without the endoscope become obvious:

A) The system 10 allows for removal of viscous secretions, semisolids and liquids without having to use the inadequately small bores of the endoscope 26 itself.

B) The system 10 will provide a system 10 heretofore unavailable to the GI endoscopist for simultaneous lavage and endoscopic visualization and treatment.

C) Removal of larger-sized material than currently possible can be accomplished with this system 10.

D) The ability to remove and replace the endoscope 26 into the system 10 while still in place anatomically will allow it to act as a protecting shield against damage of surrounding GI structures when foreign bodies are removed from the GI tract. This system 10 will also protect the upper airway as well preventing dangerous aspiration of material into the lungs.

E) This system 10 may be used for lavage of foreign material in the absence of an endoscope.

F) This system 10 in modified form can be used with colonoscopy for visualization of the lower GI tract for cleansing of stool and blood to aid in endoscopic diagnosis and treatment. No other system 10 exists with this capability.

G) No other system 10 exists which can be placed endoscopically and used independently of the endoscope 26 to draw gas and fluids from the lower GI tract providing the only such system 10 for simultaneous endoscopic diagnosis and treatment, along with decompression useful in treatment of certain common disorders. The system 10 may be left in place without the endoscope 26 to allow for continued drainage and decompression, a technique heretofore impossible to perform.

H) This system 10 can be used in conjunction with endoscopic laser therapy to remove smoke, blood and burned tissue while simultaneously performing the therapy. No other system 10 has this capability.

The manner of use of the invention with a GI endoscope 26 is a new therapeutic approach, but straightforward in concept. The proximal end of the endoscope 26 is introduced through the docking collar 66 and the whole endo scope 26 advanced forward toward the proximal end 38 of the flexible tube 14. The endoscope 26 is advanced until the flexible segment of the endoscope handle 70 makes a snug air- and water-tight contact with the docking collar 66. A lavage hose is attached to one fitting 74a and a vacuum hose is attached to the other fitting 74b and the system 10 is now ready for use. The lavage system can be either a gravity flow bag-type infusion system or operator controlled peristaltic infusion pump. The vacuum system may use either wall type vacuum unit or portable (Gomco) type vacuum pump.

The complete system 10 is then inserted either orally or rectally (upper endoscope or colonoscope) in the conventional fashion. The exposed end of the endoscope 26 makes an excellent vehicle for the introduction of both the endoscope 26 and the invention 10. Once advanced into the GI tract (beyond the upper esophagus/sphincter or colon) the invention 10 can be readily applied to remove blood, food, mucus, foreign materials and stool. Should the volume of viscous secretions, semisolids and liquids be of large magnitude, the endoscope 26 may be removed and the docking collar 66 sealed by the cover 94 and the invention 10 used without the presence of the endoscope 26. Alternatively, by connecting the docking collar 66 to a large tube, the central bores 18, 62, 68 can be used for introduction of even larger quantities of lavage fluid and extraction of even larger particles by vacuum.

The invention 10 is advanced while attached over the endoscope 26 but may be removed without the endoscope 26 being in place. The invention 10 allows for easy reinsertion of the endoscope 26 while it is in position in the GI tract. Extraction and reinsertion capability is important not only for high volume lavage and extraction but also removal of potentially hazardous materials and foreign objects which may cause direct injury to the GI tract as well as possible aspiration into and injury to the pulmonary tract. With this invention 10 objects of almost ¾ inch can be removed.

When used with a laser the invention 10 allows use of the vacuum system to draw out fumes from burned tissue as well as blood, mucus, feces and secretions, producing a clearer field of vision for the endoscopist. The same vacuum system used for fluid extraction can be used for fume removal as well.

Accordingly, the reader will see that this system 10 allows for several enhancements in the performing of GI endoscopy. It is a unique system 10 which is presently not in existence and is capable of:

A) Optimal removal of blood, food, secretions and other materials from the GI tract, leaving the bores of the endoscope 26 free to be used for their primary role as conduits for diagnostic and therapeutic devices.

B) Use concomitantly with endoscopy, allowing instillation of lavage fluid and removal of waste while performing endoscopy.

C) Removal of foreign bodies, meat and vegetable materials from the GI tract with rapid and easy insertion and removal of the endoscope.

D) Removal of harmful fluids and foreign bodies from the GI tract while preventing injury to the GI tract and pulmonary system.

E) Use as an instrument for lavage with or without endoscope in place.

F) Use in the lower GI tract (color and lower ileum) to perform simultaneous lavage and clearance of materials (blood, stool, mucus, undigested food) while performing endoscopic examination and manipulation.

G) Use in lower GI tract independently of the endoscope for removal of solids, liquids and gas for medical treatment of volvulus and ileus.

H) Use for removal of gas, blood and secretions from the GI tract while performing laser therapy.

The system 10 presented is unique from all other GI lavage systems in that it can be performed simultaneously with diagnostic and therapeutic endoscopy. Present endoscopic and lavage system function independently both physically and temporally with respect to endoscopic evaluation and therapy and lavage. No system exists which can do both at the same time, a definite benefit to the utility of endoscopy as well as its safe performance.

The present system is designed to be used with upper and lower endoscopes commonly used in clinical practice.

The following reference numerals are used on FIGS. 1 through 7:
  10 This invention
  14 Flexible tube
  18 Bore through flexible tube
  22 Tube portion of endoscope
  26 Endoscope
  30 Space between wall of bore and endoscope tube
  34 Wall of bore
  38 Proximal end of flexible tube
  42 Distal end of flexible tube
  46 Housing
  48 Hollow center of housing in alternate embodiment
  50 Proximal end of housing
  54 Distal end of housing
  58a,b Peripheral bores in housing
  62 Central bore through housing
  66 Docking collar
  68 Central bore through docking collar in alternate embodiment
  70 Endoscope head
  74a,b Tube connection fittings
  78 Proximal portion of tube
  82 Fenestration
  86 Medial, pleated portion of tube
  90 Distal portion of tube
  94 Sealing cap Thus, the present invention 10 has been described herein with reference to particular embodiments for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A method of performing gastrointestinal lavage comprising the steps of:

providing a tube having a proximal end, a distal end, a flexible section intermediate said proximal end and said distal end, a rigid, expanded section at said distal end, and a main central bore configured to loosely receive a endoscope tube, said proximal end being configured to slide into a gastrointestinal tract, said flexible section intermediate said proximal end and said distal end including a surface defining a medial pleat configured to allow said tube to flex backwards up to about 180° without collapsing said main central bore, said rigid, expanded end section including a distal central bore in communication with said main central bore, and said rigid, expanded end section including a plurality of peripheral bores in communication with said distal central bore and configured to connect a lavage tube and a vacuum tube to said distal central bore;

attaching a rubber collar around said distal end of said tube forming an air- and water-tight seal with said distal central bore, said rubber collar having a central bore and being configured to form an air- and water-tight seal with at least a portion of the endoscope;

capping said rubber collar with a cap to form an air- and water-tight seal at said distal end of said tube over said central bore of said rubber collar to seal said main central bore at said end of said tube to allow gastrointestinal lavage without the endoscope received in said main central bore;

connecting the lavage tube to one of said peripheral bores;

connecting the vacuum tube to the other of said peripheral bores;

inserting said apparatus into a gastrointestinal tract; and manually controlling said apparatus to apply at least one of lavage from said lavage tube and vacuum from said vacuum tube through said proximal end of said tube within said gastrointestinal tract without the endoscope received in said main central bore.

2. The method of claim 1, wherein said flexible section further has a plurality of fenestrations including a frontal opening and a radial opening at a proximal end of the flexible section, and wherein lavage is provided through said frontal opening and said radial opening of said plurality of fenestrations.

* * * * *